(12) United States Patent
Itoh et al.

(10) Patent No.: US 8,030,443 B2
(45) Date of Patent: Oct. 4, 2011

(54) SQUAMOUS CELL CARCINOMA ANTIGEN-DERIVED PEPTIDE BINDING TO HLA-A24 MOLECULE

(75) Inventors: Kyogo Itoh, Miyaki-gun (JP); Mamoru Harada, Fukuoka (JP)

(73) Assignee: Kurume University, Fukuoka (JP)

( * ) Notice: Subject to any disclaimer, the term of this patent is extended or adjusted under 35 U.S.C. 154(b) by 203 days.

(21) Appl. No.: 11/990,205

(22) PCT Filed: Jul. 27, 2006

(86) PCT No.: PCT/JP2006/314896
§ 371 (c)(1),
(2), (4) Date: May 7, 2009

(87) PCT Pub. No.: WO2007/018047
PCT Pub. Date: Feb. 15, 2007

(65) Prior Publication Data
US 2009/0312264 A1    Dec. 17, 2009

(30) Foreign Application Priority Data

Aug. 9, 2005    (JP) ................................ 2005-230657

(51) Int. Cl.
C07K 5/00    (2006.01)
(52) U.S. Cl. ..................................................... 530/300
(58) Field of Classification Search .................. None
See application file for complete search history.

(56) References Cited

U.S. PATENT DOCUMENTS
6,555,652 B1 *    4/2003    Itoh et al. ...................... 530/328

FOREIGN PATENT DOCUMENTS
EP    1 640 018    3/2006
WO    00/09075    2/2000
WO    WO0142277    *    6/2001

OTHER PUBLICATIONS

Harig et al., Blood, vol. 98, p. 2999-3005, 2001.*
Mine et al, Cancer Sci, 94:548-556, 2003.*
Schineider et al., PNAS, vol. 92, p. 3147-51, 1995.*
Sequence search result (U19556), 2010.*
International Search Report issued Oct. 10, 2006 in corresponding International (PCT) Application No. PCT/JP2006/314896.
Supplemental European Search Report issued Sep. 25, 2009 in corresponding European Application No. PCT/JP2006/314896.
Kato et al; "Radioimmunoassay for Tumor Antigen of Human Cervical Squamous Cell Carcinoma"; Cancer, American Cancer Society; Philadelphia, PA, US; vol. 40, No. 4; c. Jan. 1977; p. 1621-1628.
Masahide et al; "Immunotherapy and gene therapy of cancer using antibodies or their genes against tumor-associated antigens"; Anticancer Research, International Institute of Anticancer Research, GR; vol. 23, No. 6a, c. Nov. 2003; p. 4377-4381.
Kuroki et al.; "Significance of tumor-associated antigens in the diagnosis and therapy of cancer: An overview" Anticancer Research, International Institute of Anticancer Research, GR, vol. 22, No. 6C, Jan. 2002; p. 4255-4264.
Ito et al.; "7-: Gan KogenPeptide Vaccine Idenshi Dotei kara Rinsho Kenkyu e"; Nichigai Kaishi, c. Jan. 2000; vol. 101, No. 9; p. 612-617.
Tahara et al.; "Identification of a MAGE-2-encoded human leukocyte antigen-A24-binding synthetic peptide that induces specific antitumor cytotoxic T lymphocytes"; Clinical Cancer Research; c. 1999; vol. 5, No. 8; p. 2236-2241.
Toyoshima et al.; "Koku Henpei Johi Gan Kanja ni Okeru Shuyo Shui no Lymphocyte Shinjun to Koshuyo Saibo Shogaisei T Saibo no in vitro Yudo tono Kanren"; 63rd Annual Meeting of the Japan Cancer Association Kiji; c. Aug. 2004; p. 301; (lecture No. P-0763).
Kamura, "Fujinka Gan Peptide Vaccine no Rinsho Kenkyu ni Kansuru Kenkyu"; Kosei Rodo Kagaku Kenkyu Kenkyuhi Hojokin Kiso Kenkyu Seika no Rinsho Oyo Suishin Kenkyu Jigyo Gan Chiryo Peptide Vaccine Dyobi Peptide Kotai Kaihatsu: Idenshi Dotei kara Rinsho Shiken Madeni Kansuru Kenkyu; c. May 2005; Heisei 16 Nendo Sokatsu Kenkyu Hokokusho; p. 23-25.
Fumiaki Tanaka et al., "Jujo Saibo o Mochiita Gan Tokui Men'eki Chiryo"; Gendai Iryo; c. Jul. 2004; vol. 36, No. 7; p. 191-195.
Schneider et al.; "Human squamous cell carcinoma antigen 1 (8CCA1) mRNA"; c. Nov. 1995; NCBI Entrez Nucleotide, Accession U19556; Retrieved from the internet:<URL:http://www.ncbi.nlm.nih.gov/entrez/viewer.fcgi?1052868: OLDID:1802152.
Yamanaka; "Akusei Shinkei Koshu ni Taisuru Peptide Vaccine no Rinsho Kenkyu ni Kansuru Kenkyu", Kosei Rodo Kagaku Kenkyu Kenkyuhi Hojokin Kiso Kenkyu Seika no Rinsho Oyo Suishin Kenkyu Jigyo Gan Chiryo Peptide Vaccine Oyobi Peptide Kotai Kaihatsu: Idenshi Dotei kara Rinsho 8hiken Madeni Kansuru Kenkyu; c. May 2005; Heisei 16 Nendo Sokatsu Kenkyu Hokokusho; p. 45-48.
M1MURA et al.; "HLA-A24 Kosokusei HER2 Epitope Dotei to Gan Vaccine Ryoho"; Japanese Journal of Cancer and Chemotherapy, Oct. 2003; vol. 30, No. 11, p. 1802-1804.
Hagihara et al.; "The in vitro generation of Ph1+ALL-specific HLA-A24-restricted cytotoxic T lymphocytes using a synthetic 16 mer minor bcr-abl peptide"; Leukemia Research; c. 2003, vol. 27, No. 3, p. 253-257.
Nishiyama et al.; "Immunotherapy of bladder cancer using autologous dendritic cells pulsed with human lymphocyte antigenA24-specific MAGE-3 peptide"; Clinical Cancer Research; c. 2001; vol. 7, No. 1; p. 23-31.
Parker et al.; "Scheme for ranking potential HLA-A2 binding peptides based on independent binding of individual peptide sidechains"; The Journal of Immunology; c. 1994; vol. 152, No. 1, p. 163-175.
Homma et al.; "Identification of Squamous Cell Carcinoma Antigen-Derived Peptides Having the Capacity of Inducing Cancer-Reactive CTLs in HLA-A24+ Cancer Patients"; International Journal of Oncology; c. 2006; vol. 29, No. 3; p. 577-587.
Kato et al; "Radioimmunoassay for Tumor Antigen of Human Cervical Squamous Cell Carcinoma"; Cellular & Molecular Biology; c. 1979; No. 25; p. 51-56.

(Continued)

*Primary Examiner* — Misook Yu
*Assistant Examiner* — Lei Yaolei Yao
(74) *Attorney, Agent, or Firm* — Wenderoth, Lind & Ponack, L.L.P.

(57) ABSTRACT

Provided is a squamous cell carcinoma antigen derived peptide which is capable of binding to an HLA-A24 molecule and recognized by the cellular immune system, and a pharmaceutical composition comprising said peptide for the treatment or prevention of squamous cell carcinoma.

2 Claims, 5 Drawing Sheets

OTHER PUBLICATIONS

Takeshima et al.; "Origin of CA125 and SCC Antigen in Human Amniotic Fluid"; Asia-Oceania Journal of Obstetrics/Gynecology; c. 1993; vol. 19, No. 2; p. 199-204.

Kato et al; "Tumor Antigen of Human Cervical Squamous Cell Carcinoma"; Cancer, American Cancer Society; Philadelphia, PA, US; vol. 43; c. 1979; p. 585-590.

Lara et al.; "The Role of Squamous Cell Carcinoma Antigen in the Management of Laryngeal and Hypopharyngeal Cancer"; Cancer; c. Sep. 1995; vol. 76, No. 5; p. 758-764.

Snyderman et al.; "A Reappraisal of the Squamos Cell Carcinoma Antigen as Tumor Marker in Head and Neck Cancer"; Arch Otolaryngol Head Neck Surgery; c. Nov. 1995; vol. 121; p. 1294-1297.

Hefler et al; "Serum Concentrations of Squamous Cell Carcinoma Antigen in Patients with Vulvar Intraepithelial Neoplasia and Vulvar Cancer"; Int. Journal of Cancer (Fred. Oncol.); Wiley-Liss, Inc.; c. 1999; vol. 84; p. 299-303.

Senekjian et al.; "An Evaluation of Squamous Cell Carcinoma Antigen in Patients with Cervical Squamous Cell Carcinoma"; American Journal for Obstetrics and Gynecology; c. 1987; vol. 157; p. 433-439.

Duk et al.; "Cancer of the Uterine Cervix: Sensitivity and Specificity of Serum Squamous Cell Carcinoma Antigen Determinations"; Gynecological Oncology; c. 1990; vol. 39; p. 186-194.

Bolli et al.; "Squamous Cell Carcinoma Antigen: Clinical Utility in Squamous Cell Carcinoma of the Uterine Cervix"; Gynecological Oncology; c. 1994; vol. 55; p. 169-173.

Daver et al.; "Intérêt diagnostique du dosage du SCC-TA4 dans quatre localisations de cancers épidermoïdes. Expérience di sous-groupe de radio-analyse de la FNCLCC"; Bull Cancer; Elsevier, Paris; c. 1990; vol. 77; p. 781-792.

Bolger et al.; "Prognostic Value of Preoperative Squamous Cell Carcinoma Antigen Level in Patients Surgically Treated for Cervical Carcinoma"; Gynecological Oncology; Academic Press; c. 1997; vol. 65; Article No. G0974619; p. 309-313.

Ito et al.; "Molecular Basis of T Cell-mediated Recognition of Pancreatic Cancer Cells"; Cancer Research; c. Mar. 2001; vol. 61; p. 2038-2046.

Shichijo et al.; "A Gene Encoding Antigenic Peptides of Human Squamous Cell Carcinoma Recognized by Cytotoxic T Lymphocytes"; The Journal of Experimental Medicine; The Rockefeller University Press; c. 1998; vol. 187, No. 3; p. 277-288.

Yang et al.; "Identification of a Gene Coding for a Protein Possessing Shared Tumor Epitopes Capable of Inducing HLA-A24-restricted Cytotoxic T Lymphocytes in Cancer Patients"; Cancer Research; c. Aug. 1999; vol. 59; p. 4056-4063.

Noguchi et al.; "Induction of Cellular and Humoral Immune Responses to Tumor Cells and Peptides in HLA-A24 Positive Hormone-Refractory Prostate Cancer Patients by Peptide Vaccination"; Prostate; Wiley-Liss, Inc.; c. 2003; vol. 57; pp. 80-92.

Sato et al.; "Immunological Evaluation of Peptide Vaccination for Patients with Gastric Cancer Based on Pre-Existing Cellular Response to Peptide"; Cancer; c. Sep. 2003; vol. 94, No. 9; p. 802-808.

Mine et al.; "Immunological Evaluation of CTL Precursor-Oriented Vaccines for Advanced Lung Cancer Patients"; Cancer Science; c. Jun. 2003; vol. 94, No. 6; p. 548-556.

Tsuda et al.; "Vaccination with Predesignated or Evidence-Based Peptides for Patients with Recurrent Gynecologic Cancers"; Journal of Immunotherapy; Lippincott Williams & Wilkins; c. Jan. 2004; vol. 27, No. 2; p. 60-72.

Mine et al.; "Humoral Responses to Peptides Correlate with Overall Survival in Advanced Cancer Patients Vaccinated with Peptides Based on Pre-Existing, Peptide-Specific Cellular Responses"; Clinical Cancer Research; c. Feb. 2004; vol. 10; p. 929-937.

* cited by examiner

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial
<220> FEATURE:
<223> OTHER INFORMATION: SCCA 10-19 peptide

<400> SEQUENCE: 1

Lys Phe Met Phe Asp Leu Phe Gln Gln Phe
1               5                   10

<210> SEQ ID NO 2
<211> LENGTH: 9
<212> TYPE: PRT
<213> ORGANISM: Artificial
<220> FEATURE:
<223> OTHER INFORMATION: SCCA 84-92 peptide

<400> SEQUENCE: 2

Gln Phe Gln Lys Leu Leu Thr Glu Phe
1               5

<210> SEQ ID NO 3
<211> LENGTH: 10
<212> TYPE: PRT
<213> ORGANISM: Artificial
<220> FEATURE:
<223> OTHER INFORMATION: SCCA 98-107 peptide

<400> SEQUENCE: 3

Ala Tyr Glu Leu Lys Ile Ala Asn Lys Leu
1               5                   10

<210> SEQ ID NO 4
<211> LENGTH: 10
<212> TYPE: PRT
<213> ORGANISM: Artificial
<220> FEATURE:
<223> OTHER INFORMATION: SCCA 107-116 peptide

<400> SEQUENCE: 4

Leu Phe Gly Glu Lys Thr Tyr Leu Phe Leu
1               5                   10

<210> SEQ ID NO 5
<211> LENGTH: 9
<212> TYPE: PRT
<213> ORGANISM: Artificial
<220> FEATURE:
<223> OTHER INFORMATION: SCCA 112-120 peptide

<400> SEQUENCE: 5

Thr Tyr Leu Phe Leu Gln Glu Tyr Leu
1               5
```

```
<210> SEQ ID NO 6
<211> LENGTH: 9
<212> TYPE: PRT
<213> ORGANISM: Artificial
<220> FEATURE:
<223> OTHER INFORMATION: SCCA 118-126 peptide

<400> SEQUENCE: 6

Glu Tyr Leu Asp Ala Ile Lys Lys Phe
1               5

<210> SEQ ID NO 7
<211> LENGTH: 10
<212> TYPE: PRT
<213> ORGANISM: Artificial
<220> FEATURE:
<223> OTHER INFORMATION: SCCA 215-224 peptide

<400> SEQUENCE: 7

Gln Tyr Thr Ser Phe His Phe Ala Ser Leu
1               5                   10

<210> SEQ ID NO 8
<211> LENGTH: 10
<212> TYPE: PRT
<213> ORGANISM: Artificial
<220> FEATURE:
<223> OTHER INFORMATION: SCCA 286-295 peptide

<400> SEQUENCE: 8

Arg Phe Lys Val Glu Glu Ser Tyr Asp Leu
1               5                   10

<210> SEQ ID NO 9
<211> LENGTH: 9
<212> TYPE: PRT
<213> ORGANISM: Artificial
<220> FEATURE:
<223> OTHER INFORMATION: SCCA 362-370 peptide

<400> SEQUENCE: 9

Glu Phe His Cys Asn His Pro Phe Leu
1               5

<210> SEQ ID NO 10
<211> LENGTH: 10
<212> TYPE: PRT
<213> ORGANISM: Artificial
<220> FEATURE:
<223> OTHER INFORMATION: HIV peptide

<400> SEQUENCE: 10

Arg Tyr Leu Arg Gln Gln Leu Leu Gly Ile
1               5                   10

<210> SEQ ID NO 11
<211> LENGTH: 390
<212> TYPE: PRT
<213> ORGANISM: Artificial Sequence
<220> FEATURE:
<223> OTHER INFORMATION: Synthetic construct

<400> SEQUENCE: 11

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
                20                  25                  30
```

-continued

```
Ser Ile Thr Ser Ala Leu Gly Met Val Leu Leu Gly Ala Lys Asp Asn
        35                  40                  45
Thr Ala Gln Gln Ile Lys Lys Val Leu His Phe Asp Gln Val Thr Glu
    50                  55                  60
Asn Thr Thr Gly Lys Ala Ala Thr Tyr His Val Asp Arg Ser Gly Asn
65                  70                  75                  80
Val His His Gln Phe Gln Lys Leu Leu Thr Glu Phe Asn Lys Ser Thr
                85                  90                  95
Asp Ala Tyr Glu Leu Lys Ile Ala Asn Lys Leu Phe Gly Glu Lys Thr
            100                 105                 110
Tyr Leu Phe Leu Gln Glu Tyr Leu Asp Ala Ile Lys Lys Phe Tyr Gln
        115                 120                 125
Thr Ser Val Glu Ser Val Asp Phe Ala Asn Ala Pro Glu Glu Ser Arg
    130                 135                 140
Lys Lys Ile Asn Ser Trp Val Glu Ser Gln Thr Asn Glu Lys Ile Lys
145                 150                 155                 160
Asn Leu Ile Pro Glu Gly Asn Ile Gly Ser Asn Thr Thr Leu Val Leu
                165                 170                 175
Val Asn Ala Ile Tyr Phe Lys Gly Gln Trp Glu Lys Lys Phe Asn Lys
            180                 185                 190
Glu Asp Thr Lys Glu Glu Lys Phe Trp Pro Asn Lys Asn Thr Tyr Lys
        195                 200                 205
Ser Ile Gln Met Met Arg Gln Tyr Thr Ser Phe His Phe Ala Ser Leu
    210                 215                 220
Glu Asp Val Gln Ala Lys Val Leu Glu Ile Pro Tyr Lys Gly Lys Asp
225                 230                 235                 240
Leu Ser Met Ile Val Leu Leu Pro Asn Glu Ile Asp Gly Leu Gln Lys
                245                 250                 255
Leu Glu Glu Lys Leu Thr Ala Glu Lys Leu Met Glu Trp Thr Ser Leu
            260                 265                 270
Gln Asn Met Arg Glu Thr Arg Val Asp Leu His Leu Pro Arg Phe Lys
        275                 280                 285
Val Glu Glu Ser Tyr Asp Leu Lys Asp Thr Leu Arg Thr Met Gly Met
    290                 295                 300
Val Asp Ile Phe Asn Gly Asp Ala Asp Leu Ser Gly Met Thr Gly Ser
305                 310                 315                 320
Arg Gly Leu Val Leu Ser Gly Val Leu His Lys Ala Phe Val Glu Val
                325                 330                 335
Thr Glu Glu Gly Ala Glu Ala Ala Ala Thr Ala Val Val Gly Phe
            340                 345                 350
Gly Ser Ser Pro Thr Ser Thr Asn Glu Glu Phe His Cys Asn His Pro
        355                 360                 365
Phe Leu Phe Phe Ile Arg Gln Asn Lys Thr Asn Ser Ile Leu Phe Tyr
    370                 375                 380
Gly Arg Phe Ser Ser Pro
385                 390
```

US 8,030,443 B2

SQUAMOUS CELL CARCINOMA ANTIGEN-DERIVED PEPTIDE BINDING TO HLA-A24 MOLECULE

This application is a U.S. national stage of International Application No. PCT/JP2006/314896 filed Jul. 27, 2006.

FIELD OF THE INVENTION

The instant invention relates to peptides which are derived from squamous cell carcinoma antigen (SCCA) and are useful for the specific immunotherapy for HLA-A24+ Squamous Cell Carcinoma (SCC) patient.

SCCA is a cancer related antigen which expressed on squamous cell carcinomas (SCCs) (Non patent literature 1). Although SCCA was detected in normal squamous epithelium as well as saliva, respiratory secretions, and amniotic fluid samples from healthy individuals (Non-patent literatures 2, 3), it has also been deemed as a useful marker for SCC(Non patent literature 4). SCCA is currently used to predict disease-free and overall survival rate in head and neck, lung, and vulvar SCCs (Non-patent literatures 5-7). In addition, several studies have confirmed that elevated SCCA levels correlate well with the extent of disease in patients with cervical SCC (Non-Patent Literatures 8-12). These lines of evidence suggest that SCCA could be a promising candidate molecule in the development of anti-tumor immunotherapy.

The present inventors have already identified various cancer-related antigens and their epitope peptides that are recognized by cancer-reactive cytotoxic T lymphocytes (CTLS) (Non-patent literatures 13-15), and conducted clinical trials of peptide-based vaccines against various types of cancers (Non-patent literatures 16-19). In such trials, some of the CTL-directed peptides tested have been exhibited the ability to elicit both cellular and humoral immune responses in vivo. In addition, the levels of anti-peptide antibodies in post-vaccination sera were closely correlated with the overall survival rate of advanced cancer patients who had received a peptide vaccination (Non-patent literature 20).

[Non-Patent Literature 1] Kato H, Torigoe T. Radioimmunoassay for tumor antigen of human cervical squamous cell carcinoma. Cancer 1977; 40:1621-8.

[Non-Patent literature 2] Kato H, Morioka H, Aramaki S, Torigoe T. Radioimmunoassay for tumor-antigen of human cervical squamous cell carcinoma. Cell Mol Biol 1979; 25:51-6.

[Non-Patent literature 3] Takeshima S, Suminami Y, Takeda O, Abe H, Kato H. Origin of CA125 and SCC antigen in human amniotic fluid. Asia Oceania J Obstet Gynaecol 1993; 19:199-204.

[Non-Patent literature 4] Kato H, Miyauchi F, Morioka H, Fujino T, Torigoe T. Tumor antigen of human cervical squamous cell carcinoma: correlation of circulation levels with disease progress. Cancer 1979; 43:585-90.

[Non-Patent literature 5] Lara P C, Cuyas J M. The role of squamous cell carcinoma antigen in the management of laryngeal and hypopharyngeal cancer. Cancer 1995; 76:758-64.

[Non-Patent literature 6] Snyderman C H, D'Amico F, Wagner R, Eibling D E. A reappraisal of the squamous cell carcinoma antigen as a tumor marker in head and neck cancer. Arch Otolaryngol Head Neck Surg 1995; 121:1294-7.

[Non-Patent literature 7] Hefler L, Obermair A, Tempfer C, et al. Serum concentration of squamous cell carcinoma antigen in patients with vulvar intraepithelial neoplasia and velvar cancer. Int J Cancer 1999; 84 :299-303.

[Non-Patent literature 8] Senekjian E K, Young J M, Weiser P A, Spencer C E, Magic S E, Herbst A L. An evaluation of squamous cell carcinoma antigen in patients with cervical squamous cell carcinoma. Am J Obstet Gynecol 1987; 157:433-9.

[Non-Patent literature 9] Duk J M, de Bruijn H W A, Groenier K H, et al. Cancer of the uterine cervix: sensitivity and specificity of serum squamous cell carcinoma antigen determinations. Gynecol Oncol 1009; 89:186-94.

[Non-Patent literature 10] Bolli J A, Doering D L, Bosscher J R, et al. Squamous cell carcinoma antigen: clinical utility in squamous cell carcinoma of the uterine cervix. Gynecol Oncol 1994; 55:169-73.

[Non-Patent literature 11] Daver A, Dalifard I, Pons-Anicet D, et al. Diagnosis value of SCC-TA-4 determination in 4 localizations of epidermoid cancers. An experience of the FNCLCC subgroup of ratio-analysis. Bull Cancer 1990; 77:781-92.

[Non-Patent literature 12] Bolger B S, Dabbas M, Lopes A, Monaghan J M. Prognostic value of preoperative squamous cell carcinoma antigen level in patients surgically treated cervical carcinoma. Gynecol Oncol 1997; 65:309-13.

[Non-Patent literature 13] Ito M, Shichijo S, Tsuda N, Ochi M, Harashima N, Saito N, Itoh K. Molecular basis of T cell-mediated recognition of pancreatic cancer cells. Cancer Res 2001; 61: 2038-46.

[Non-Patent literature 14] Shichijo S, Nako M, Imai Y, et al. A gene encoding antigenic peptides of human squamous cell carcinoma recognized by cytotoxic T lymphocytes. J Exp Med 1998; 187:277-88.

[Non-Patent literature 15] Yang D, Nako M, Shichijo S, et al. Identification of a gene coding for a protein possessing shared tumor epitope capable of inducing HLA-A24-restricted cytotoxic T lymphocytes in cancer patients. Cancer Res 1999; 59:4056-63.

[Non-Patent literature 16] Noguchi M, Kobayashi K, Suetsugu N, et al. Induction of cellular and humoral immune responses to tumor cells and peptides in HLA-A24 positive hormone-refractory squamous cell carcinoma patients by peptide vaccination. Prostate 2003; 57: 80-92.

[Non-Patent literature 17] Sato Y, Shomura H, Maeda Y, et al. Immunological evaluation of peptide vaccination for patients with gastric cancer based on pre-existing cellular response to peptide. Cancer Sci 2003; 94: 802-8.

[Non-Patent literature 18] Mine T, Gouhara R, Hida N, et al. Immunological evaluation of CTL precursor-oriented vaccines for advanced lung cancer patients. Cancer Sci 2003; 94: 548-56.

[Non-Patent literature 19] Tsuda N, Mochizuki K, Harada M, et al. Vaccination with predesignated or evidence-based peptides for patients with recurrent gynecologic cancers. J Immunother 2004; 27:60-72.

[Non-Patent literature 20] Mine T, Sato Y, Noguchi M, et al. Humoral responses to peptides correlated with overall survival in advanced cancer patients vaccinated with peptides based on pre-existing, peptide-specific cellular responses. Clin. Cancer Res. 2004; 10:929-37.

The references cited in this specification including those in the above list are herein incorporated by reference.

DISCLOSURE OF THE INVENTION

Problem to be Solved by the Invention

An object of the present invention is to provide a SCCA derived peptide which is presented with HLA-A24 molecules (the allele that is found about 60% of Japanese people) and is capable of inducing CTLs against the SSC cells.

Means for Solving the Problem

The present invention provides a SCCA derived peptide which is capable of binding to an HLA-A24 molecule and recognized by the cellular immune system. Particularly, the present invention provides a peptide consisting of amino acid sequence of SEQ ID No. 5 or 7 or a derivative thereof. Further, the present invention also provides a nucleic acid molecule which encodes the peptide of the present invention and a vector comprising the nucleic acid molecule.

The present invention further provides a pharmaceutical composition, especially provide the composition of cancer vaccine, for the treatment or prevention of SCC comprising the peptide, peptide derivative or vector of the present invention.

The present invention further provides a method for the treatment or prevention of SCC, which comprises administering the peptide, peptide derivative or vector of the present invention to a subject to be treated. According to the method of the present invention, the peptide, peptide derivative or vector is preferably administered as cancer vaccine.

The present invention also provide use of the peptide, peptide derivative or vector of the present invention for the manufacture of a pharmaceutical composition, especially a cancer vaccine, for the treatment or prevention of SCC.

The present invention further provides a method for inducing CTL against SCC, which comprises contacting peripheral blood mononuclear cell (PBMC) isolated from a HLA-A24$^+$ SCC patient with the peptide or peptide derivative of the present invention.

Further more, the present invention provides a method for the preparation of an antigen presenting cell which presents a complex between the SCC related antigen derived peptide or a derivative thereof and a HLA-A24 molecule on the surface of the cell, which comprises allowing a cell having antigen-presenting ability isolated from a HLA-A24$^+$ SCC patient to be incorporated with the peptide, peptide derivative or vector of the present invention.

Effect of the Invention

According to the present invention, SCCA derived peptide which can induce CTL being capable of killing cancer cells expressing SCCA in an HLA A24$^+$ SCC patient is provided. According to the present invention, specific immunotherapy for a HLA-A24$^+$ SCC patient became possible. The specific immunotherapy of the present invention is applicable for a substantial number of cancer patients, as SCC accounts for the majority of epithelium-derived neoplastic cells.

BEST MODE FOR CARRYING OUT THE INVENTION

Figure 1:
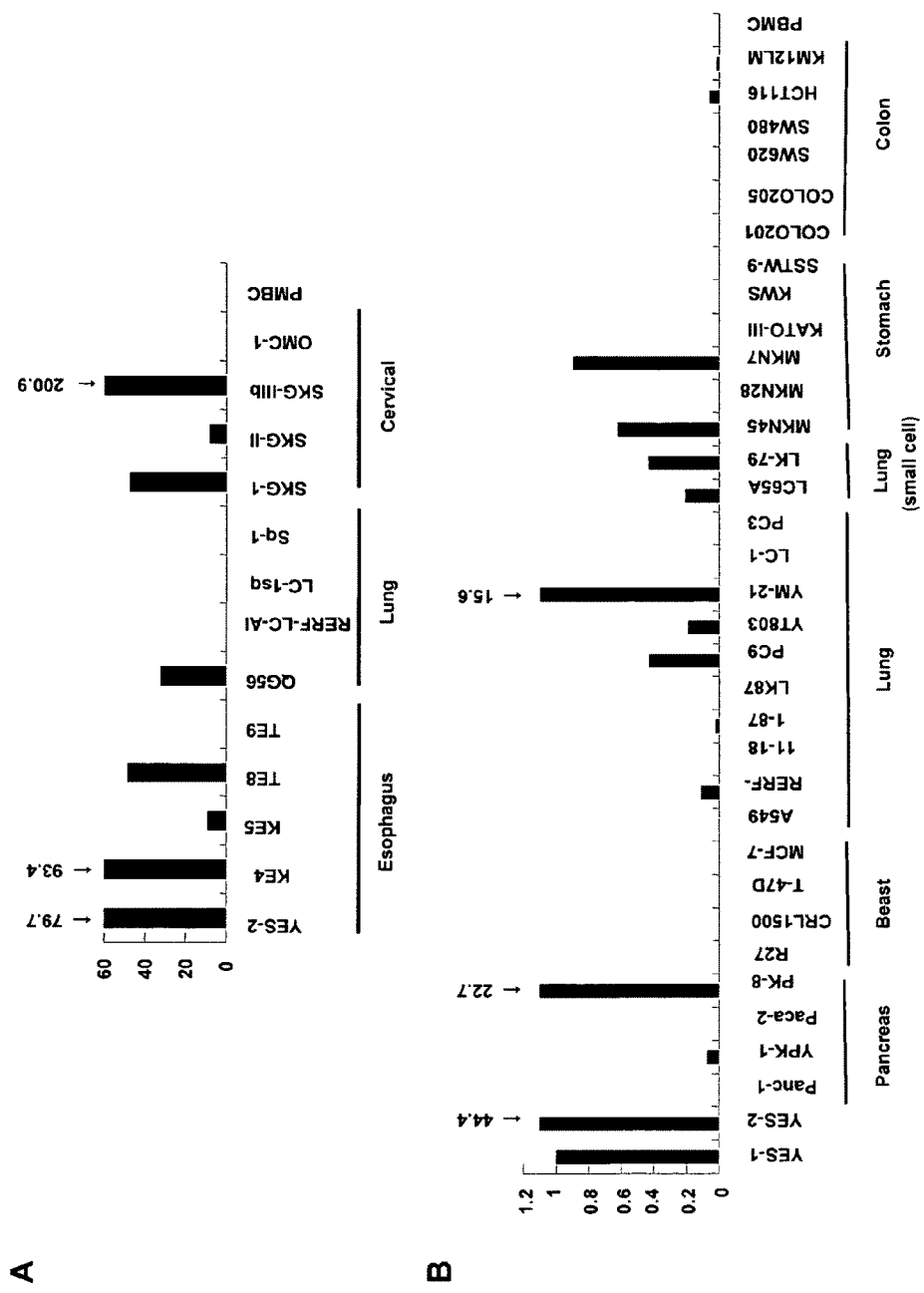
FIG. 1 Expression of SCCA mRNA in various SCC and non-SCC cell lines. A represents results of SCC lines and B is of non-SCC lines. The values on the axis and the top of the graph represent relative expression of the SCCA mRNA of the samples when the SCCA mRNA expression in YES-1 was considered as expression level 1.

In the present invention, "SCCA derived peptide" or "SCCA peptide" refers to a peptide fragment having an amino acid sequence which is a part of the amino acid sequence of SCCA. The amino acid sequence of SCCA has been disclosed by GenBank under accession number of U19556.

According to the invention, the phrase "a peptide is capable of binding to an HLA-A24 molecule" means that said peptide binds to an HLA-A24 molecule to form complex and the complex is presented on the cell surface. In general, peptides that are capable of binding to an HLA molecule shares some specific amino acid sequences with regularity depending on the types of the HLA. The specific amino acid sequences with regularity are called as "binding motifs". That is, the binding motif to the HLA-A24 molecule is the sequence whose amino acid next to the N-terminal of the peptide derivative is tyrosine or phenylalanine, and that at the C-terminal is iso-leucine, leucine or phenylalanine. Binding of a peptide having the binding motif to the HLA-A24 molecules to an HLA-A24 molecule can be determined using computer analysis such as Bioinformatics and Molecular Analysis Section (NIH, Bethesda, Md., Parker K C, Et al., J. Immunol., 152: 153-175, 1994).

According to the present application, the phrase "a peptide is recognized by the cellular immune system" means that the peptide is recognized by specific CTL. In other word, the peptide has an ability to induce the peptide specific CTL. The art can determine whether or not a peptide is recognized by CTL by a known method. For example, by determining whether or not a cytokine such as γ-IFN is produced by CTL in response to antigen presenting cells which are pulsed with said peptide using the ELISA technique. In addition, cytotoxic activity of the induced CTL can be determined by the $^{51}$Cr-release assay and the like. Preferred length of the amino acid sequence of the peptide of the present invention is 8 to 14, more preferably 8 to 11 and especially, 9 or 10 amino acid residues in view of good recognition by CTL.

According to the invention, the phrase "a peptide is recognized by the humoral immune system" means that an IgG specific to said peptide is present in the body. That is, the peptide-specific IgG is detected in the plasma of the subject. Peptides recognized by both the cellular and humoral immune systems are expected to exhibit higher immunogenicity in the body therefore, such peptides are preferable as peptides of the present invention. The amount of the specific IgGs can be determined by commonly known ELISA techniques and the like.

A peptide consisting of an amino acid sequence shown in SEQ ID NO: 5 or 7 is especially useful for the peptide of the invention.

According to the instant invention, "peptide derivative of a SCCA derived peptide" of the invention is a derivative that has one or two substitution in the original amino acid sequence, deletion and/or addition of one or two amino acids to the original amino acid sequence and is capable of binding to an HLA-A24 molecule and recognized by the cellar and/or humoral immune system. Whether or not a peptide derivative has the desired properties can be determined by the above-described procedures.

In order to do not alter the property of the original peptide, the substitution of amino acid residue is preferably made within the amino acids belonging to the same family, such as polar amino acids, non-polar amino acids, hydrophobic amino acids, hydrophilic amino acids, positively charged amino acids, negatively charged amino acids and aromatic amino acids. The deletion and/or addition of an amino acid are preferably made so that the number of the amino acid residues consisting the derivative is 8-11.

The substitution, deletion and/or addition of amino acid is preferably made so that the derivative is acceptable in view of HLA binding motifs. That is, the amino acid modification is preferably made so that the amino acid next to the N-terminal is tyrosine or phenylalanine and the C-terminus amino acid is isoleucine, leucine or phenylalanine.

According to the instant invention, peptide derivatives of SEQ ID No. 5 whose amino acid residue next to the N-terminal is substituted by phenylalanine and/or the C-terminus amino acid residue is substituted by isoleucine or phenylalanine as well as peptide derivatives of SEQ ID No. 7 whose amino acid residue next to the N-terminal is substituted by phenylalanine and/or the C-terminus amino acid residue is substituted by isoleucine or phenylalanine are especially preferable.

The amino acid constituting the SCCA derived peptides and the derivatives thereof according to the invention may be natural amino acids or amino acid analogues. Amino acid analogues may include N-acylated, O-acylated, esterified, acid amidated and alkylated amino acids. The amino or carboxylic group or the like of the amino acid residue constituting the peptide or a derivative thereof may be modified so long as it does not significantly deteriorate the function of the peptide. The modification may be addition of formyl, acetyl or t-butoxycarbonyl groups at the N-terminus- or free-amino group, or addition of methyl, ethyl, t-butyl or benzyl group at the C-terminus- or free carboxylic group.

The peptide and peptide derivative according to the present invention may be synthesized by a conventionally used peptide synthesizing procedure. Examples of the conventionally used procedures are those described in the literatures including "Peptide Synthesis", Interscience, New York, 1966; "The Proteins", vol. 2, Academic Press Inc., New York, 1976; "*Pepuchido-Gosei*", Maruzen Co. Ltd., 1975; "*Pepuchido-Gosei-no-Kiso-to-Jikkenn*", Maruzen Co. Ltd., 1985; and "*Iyakuhin-no-Kaihatu, Zoku*, vol. 14, *Peputido-Gosei*", Hirokawa Shoten, 1991.

The peptide and peptide derivative of the present invention may be those generated by fragmentation of a peptide containing the amino acid sequence of the peptide or peptide derivative of the present invention in a cell. The instant invention encompass the use of such peptide as above. As long as the peptide or peptide derivative of the present invention can be provided, the peptide may comprise any number of amino acid residues.

The peptide and peptide derivative of the present invention can effectively induce and growth CTLs which affect efficiently against HLA-A24$^+$ SCCA expressing cancer cells and therefore, are useful for treating various cancers which express SCCA. SCCA has been known as a tumor marker in SCC patients (Non-Patent Literature 4). In addition, the inventors have revealed that most of SCC cells express SCCA in the following example section. Accordingly, the peptides or peptide derivatives of the present invention are especially useful for the treatment of SCC. Examples of SCCs include esophageal SCC, cervical SCC and lung SCC.

The present application provides a pharmaceutical composition for the treatment or prevention of SCC comprising the peptide or peptide derivative of the present invention. The pharmaceutical composition of the present invention may comprise one peptide or peptide derivative of the present invention, or a combination of two or more peptides and/or peptide derivatives. Since CTL of a patient is an aggregate of the cells recognizing a plurality of different cancer antigen peptides, it is effective to use a plurality of the peptides or peptide derivatives of the present invention in combination. The peptide or peptide derivative of the invention may be used in combination with a cancer antigen peptide other than the peptide of the present invention.

The pharmaceutical composition of the present invention may comprise a pharmaceutically acceptable carrier or the like in addition to the peptide or peptide derivative of the present invention. Examples of the carrier may include cellulose, polypeptides acid and albumin. The pharmaceutical composition of the present invention may be formulated as liposomal preparations, particulate preparations in which the ingredient is bound to beads having a diameter of several micro meters, or preparations in which the ingredient is attached to lipids. The pharmaceutical composition of the present invention may be administered along with an adjuvant which has conventionally been used for vaccination in order to establish the immune response effectively. The composition may be administrated intradermally or subcutaneously.

The pharmaceutical composition of the present invention can be used as a cancer vaccine. The amount of the peptide or peptide derivative to be administered may be determined based on the condition of the disease to be treated, age and body weight of the respective patient. The amount of the peptide or peptide derivative of the present invention in a dosage form may be 0.0001 mg-1000 mg, preferably 0.0001 mg-100 mg, more preferably 0.001 mg-10 mg. The dosage form may preferably be administered once every several days, several weeks or several months for 1-3 years.

The present application provides a nucleic acid molecule encoding the peptide or peptide derivative of the present invention and a vector comprising said nucleic acid molecule. By introducing a vector in which the nucleic acid molecule of the invention is incorporated, in an antigen presenting cell, the peptide or peptide derivative of the invention is expressed, and a complex between the HLA and the peptide or peptide derivative of the present invention is presented on the surface of the cell. Thus obtained antigen presenting cell can effectively growth peptide-specific CTLs against SCCA expressing cancer cells.

Examples of vectors in which the nucleic acid molecule of the present invention is incorporated may include various plasmid vectors and viral vectors such as adenovirus, adeno-associated virus, retrovirus and vaccinia virus vectors (Liu M, Acres B, Balloul J M, Bizouarne N, Paul S, Slos P, Squiban P. Gene-based vaccines and immunotherapeutics. Proc Natl Acad Sci USA 101 Suppl, 14567-71, 2004). Methods for preparing vectors have been well known in the art (Molecular Cloning: A laboratory manual, 2nd ed. New York, Cold Spring Harbor Laboratory).

The vector of the present invention may be administered to a patient so that SCCA derived peptide or a derivative thereof is expressed on the antigen presenting cells in the patient. Alternatively, the vector is introduced ex vivo in a suitable cell, for example a dendric cell isolated from the patient, and then the cell is returned to the patient. Those methods are well known to the art (Hrouda D, Dalgleish A G. Gene therapy for prostate cancer. Gene Ther 3: 845-52, 1996).

The amount of the vector to be administered may vary depending on the condition of the disease to be treated, the age and body weight of the patient to be treated and the like, and may preferably be 0.1 μg-100 mg, more preferably 1 μg-50 mg as an amount of DNA. The vector may be administered, for example, intravenously, subcutaneously, or intradermally.

By the method for inducing CTL according to the present invention, CTLs which kill HLA-A24$^+$ SCCA expressing cancer cells are effectively provided. In the present invention, "SCC reactive" regarding CTLs refers the property of the CTL which can recognize the complex between the cancer antigen peptide and the HLA molecule on the SCC cells and kill the recognized cells. The method of inducing CTLs according to the present invention may be carried out for example by incubating the peripheral blood mononuclear cell (PBMC) isolated from an HLA-A24$^+$ SCC patient in vitro in the presence of the peptide or peptide derivative of the present invention. The CTLs induced by the present method are useful for the adoptive immunotherapy, i.e. for treating the cancer by returning the same into the patient from which the PBMC is isolated so that the CTLs kill the cancer cells.

The CTL inducing kit of the present invention can be used for the aforementioned method for inducing CTL. The kit of the present invention comprises one or more peptide and/or peptide derivative of the present invention. In addition, the kit may further comprises a suitable buffer, culture media and the like.

By the method for the preparation of antigen presenting cells of the present invention, antigen presenting cells which can be used for inducing CTL against HLA-A24$^+$ SCCA expressing cancer cells are provided. The method of the preparation of antigen presenting cells of the present invention may be carried out, for example, by pulsing the cells having antigen-presenting ability isolated from the HLA-A24$^+$ SCC patient with the peptide or peptide derivative of the present invention so that the cells incorporate the peptide, or peptide derivative or by introducing the vector of the present invention into said cells in a conventional manner. The cells having antigen presenting ability may be, for example, dendritic cells. Dendritic cells can be prepared from PBMC obtained from the patient by isolating the cells adhered to the culture plate of the PBMC culture and then, incubating the isolated cells in the presence of IL-4 and GM-CSF for one week. The antigen presenting cells prepared by the method of the present invention can induce CTLs that specifically recognize the complex between the peptide or peptide derivative of the present invention and the HLA molecule presented on the surface of the cells. When the antigen presenting cells of the invention are administered to the an HLA-A24$^+$ SCC patient, they can induce SCC reactive CTLs in the body of the patient.

The kit for the preparation of antigen presenting cells according to the present invention is used for carrying out the aforementioned method of the present invention. The kit of the present invention comprise one or more of the peptide and/or peptide derivative of the present invention and may further comprise a suitable buffer, culture media and the like.

As is apparent from the above description, the present application further provides a method for treating or preventing SCC, which comprises administering the peptide, peptide derivative, or vector of the invention to a patient in need thereof. In addition, the instant application also provide use of the peptide, peptide derivative or vector of the present invention for the manufacture of a pharmaceutical composition for the treatment or prevention of SCC.

The present invention is further illustrated by the following examples, but is not restricted by these examples in any way.

Examples

1. METHOD 1.1 Patients and Cell Lines

After written informed consent had been obtained from each participant, PBMCs and plasma were collected from patients with esophageal, uterine cervical, lung, gastric, colon, and breast cancer as well as healthy donors (HDs) at Kurume University Hospital. All subjects were free from human immunodeficiency virus (HIV) infection. All plasma and PBMCs were cryopreserved at −80° C. and −196° C. until use, respectively. The expression of HLA class I antigens on these PBMCs was defined by flow cytometric analysis. Anti-HLA-A24 monoclonal antibody (mAB) (One Lamdbda, Inc.) was used as the firstly antibody and FITC-conjugated-anti-mouse IgG (Cappel) was used as the secondary antibody. YES-1 and YES-2 are esophageal SCC cell lines established in Surgical Division of Yamaguchi University Hospital. The other cancer cell lines used in this study are shown in FIG. 1A (SCCs) and FIG. 1B (adenocarcinomas and lung small cell carcinomas).

1.2 Quantitative PCR.

The amount of SCCA mRNA expression was quantified by real-time PCR using ABI PRISM 7000 (Applied Biosystems, Foster City, Calif.), as previously reported (Heid C A, Stevens J, Livak K J, et al. Real time quantitative PCR. Genome Res 1996; 6:986-94). RNAs were extracted using the RNA-Bee RNA isolation reagent (Tel-Test, Inc., Friendswood, Tex.) method according to the manufacturer's instructions. The cDNA of mRNA was prepared from 5 μg of total RNA using SuperScript Preamplification System (Invitrogen) according to the manufacturer's instructions. Real-time PCR of the cDNA specimens was conducted in a total volume of 12.5 μl with 1× TaqMan Master mix (Applied Biosystems), and 1.25 µl of mixture of primers and probes. The primers and TaqMan probes used in this study were purchased from Applied Biosystems (Assay ID#: Hs00199468_m1). The thermal cycler parameters included 2 min at 50° C., 10 min at 95° C., and 40 cycles involving degeneration at 95° C. for 15 sec and annealing extension at 60° C. for 1 min. SCCA mRNA expression was standardized according to β-actin mRNA expression.

1.2 Immunohistochemistry.

Formalin-fixed, paraffin-embedded sections were deparaffinized, incubated with 0.02 U/ml α2-3,6,8-neuraminidase, Vibrio Cholerae (CALBIOCHEM EMD Biosciences, Inc., La Jolla, Calif.), in phosphate-buffered saline (PBS) at room temperature for 1 h for antigen retrieval, and then treated with 3% $H_2O_2$ in PBS to block endogenous peroxidase activity. Immunohistochemistry was performed using 1:100-diluted rabbit polyclonal antibody against SCCA½ (H-390: Santa Cruz Biotechnology, Inc., Santa Cruz, Calif.) and HISTONE, SAB-PO® kit (Nichirei Co., Ltd., Tokyo, Japan). The peroxidase reaction was developed using 3,3-diaminobenzidine tetrahydrochloride, and nuclei were counter-stained with hematoxylin.

1.4 Peptides

The SCCA-derived peptides were purchased from BioSynthesis (Lewisville, Tex.); an HIV peptide with the HLA-A24 binding motif (RYLRQQLLGI:SEQ ID No. 10) was also used as a negative control. All peptides were dissolved with dimethyl sulfoxide at a dose of 10 mg/ml.

1.5 Measurement of Anti-Peptide Antibody.

The levels of anti-peptide immunoglobulin G (IgG) were measured by the LUMINEX™ system (multiplexed flow cytometric assay) as previously reported (Komatsu N, Shichijo S, Nakagawa M, Itoh K. New multiplexed flow cytometric assay to measure anti-peptide antibody: a novel tool for monitoring immune responses to peptides used for immunization. Scand J Clin Lab Invest 2004; 64:1-11). In brief, plasma was incubated with 25 µl of peptide-coupled color-coded beads for 2 hr at room temperature on a plate shaker. After incubation, the mixture was washed with a vacuum manifold apparatus and incubated with 100 µl of biotinylated goat anti-human IgG (γ chain-specific)(BA-3080, Vector Laboratories, Burlingame, Calif., USA) for 1 h at room temperature. The plate was then washed, followed by the addition of 100 µl of streptavidin-PE (S-866, Molecular Probes, Eugene, Oreg., USA) into wells, and was incubated for 30 min at room temperature on a plate shaker. The bound beads were washed three times followed by the addition of 100 µl of Tween-PBS into each well. Fifty µl of sample was detected using the LUMINEX™ system (multiplexed flow cytometric assay). To confirm the specificity of IgG to a SCCA peptide, sample plasma was cultured in plates coated with a corresponding SCCA peptide, or with an irrelevant SCCA peptide. After the operation was repeated three times, the levels of the corresponding SCCA peptide-specific IgG in the resulting supernatant were determined by the LUMINEX™ system (multiplexed flow cytometric assay).

1.6 Induction of Peptide-Specific CTLs.

PBMCs from HLA-A24$^+$ cancer patients and HDs were used for the CTL induction assay. For the induction of peptide-specific CTLs, PBMCs (1.5×10$^5$ cells/well) were incubated with 10 µg/ml of each peptide in four different wells of a 96-well microculture plate (Nunc) in 200 µl of culture medium containing interleukin (IL)-2, as reported previously (Non-Patent Literature 18). Every 3 or 4 days, half the culture medium was removed and replaced with new medium containing the corresponding peptide (20 µg/ml) and 100 U/ml IL-2. On the 14$^{th}$ day, the cells from each well were independently harvested, washed, separated into four wells, and tested for their ability to produce interferon (IFN)-γ in response to C1R-A24 cells pulsed with a corresponding peptide or a negative control HIV peptide in the duplicate assays. C1R-A24 is an HLA-A2402-expressing subline of C1R lymphoma (Dr. M. Takiguchi, Kumamoto University, Japan). After an 18-h incubation of C1RA-24, the supernatant was collected, and the level of IFN-γ was determined by ELISA.

1.7 Assay of Cytotoxicity.

Cultured cells in wells producing IFN-γ in response to a corresponding peptide were collected and further cultured with IL-2 alone for 10-14 days in order to obtain a sufficiently large number of cells to perform a standard 6-h $^{51}$Cr-release assay. The following tumor cell lines were used as targets; YES-1 (HLA-A24$^-$ and SCCA$^+$ esophageal squamous cell carcinoma), and YES-2 (HLA -A24$^+$ and SCCA$^+$ esophageal squamous cell carcinoma). Phytohemagglutinin (PHA)-stimulated blastoid T cells were also used as a negative control. In some experiments, 20 µg/ml of anti-HLA-class I (W6/32, IgG2a) (BioLegend, Camino Santa Fe, San Diego, Calif., USA), anti-HLA-class II (H-DR-1, IgG2a) (kindly provided by Dr. Yasuji NISHIMURA, KUMAMOTO UNIVERSITY, Japan), anti-CD4 (Nu-Th/i, IgG1) (established at Department of Immunology, Kurume University School of Medicine, Japan), or anti-CD8 (Nu-Ts/c, IgG2a) monoclonal antibody (mAb) (established at Department of Immunology, Kurume University School of Medicine, Japan) were added to the wells at the initiation of the assay. An anti-CD14 (JML-H14, IgG2a) mAb (established at Department of Immunology, Kurume University School of Medicine, Japan) was used as a negative control. In a cold-inhibition assay, unlabeled C1R-A24 cells which were pre-pulsed with the corresponding SCCA peptide or an HIV peptide were added into the wells at a cold/hot target cell ratio of 10/1.

1.8 Statistics

A two-tailed Student's t-test was employed for the statistical analysis.

2. RESULTS 2.1 Expression of SCCA mRNA in Various Types of SCCs and Non-SCCs

First, the SCCA expression in a panel of SCC lines was investigated. The amount of expression of SCCA mRNA was determined by the real-time PCR method. The expression of SCCA mRNA in SCC YES-1 was considered to be expression level 1, and the relative expression of SCCA mRNA was also shown. As a result, the SCCA mRNA was found to be expressed in 4 of 5 esophageal cancer cell lines, 1 of 4 lung cancer cell lines, and 3 of 4 cervical cancer cell lines tested, respectively (FIG. 1A).

Further, whether or not SCCA is expressed in non-SCC lines because no report has described SCCA expression in non-SCCs was determined. All cancer cell lines, with the exception of two lung small cell carcinoma lines, were adenocarcinoma. SCCA mRNA was found to be expressed in 2 of 4 pancreatic cancer cell lines, 4 of 10 lung cancer cell lines, 2 of 6 gastric cancer cell lines, and 1 of 6 colon cancer cell lines tested (FIG. 1B). Both lung small cell carcinoma cell lines were positive for SCCA mRNA expression, but all 4 breast adenocarcinoma cell lines were negative for it. Its expression in normal PBMCs was negative. In general, the level of SCCA mRNA expression was higher in SCC lines than in non-SCC lines.

2.2 Expression of SCCA in SCC and Non-SCC Tissues

Figure 2:
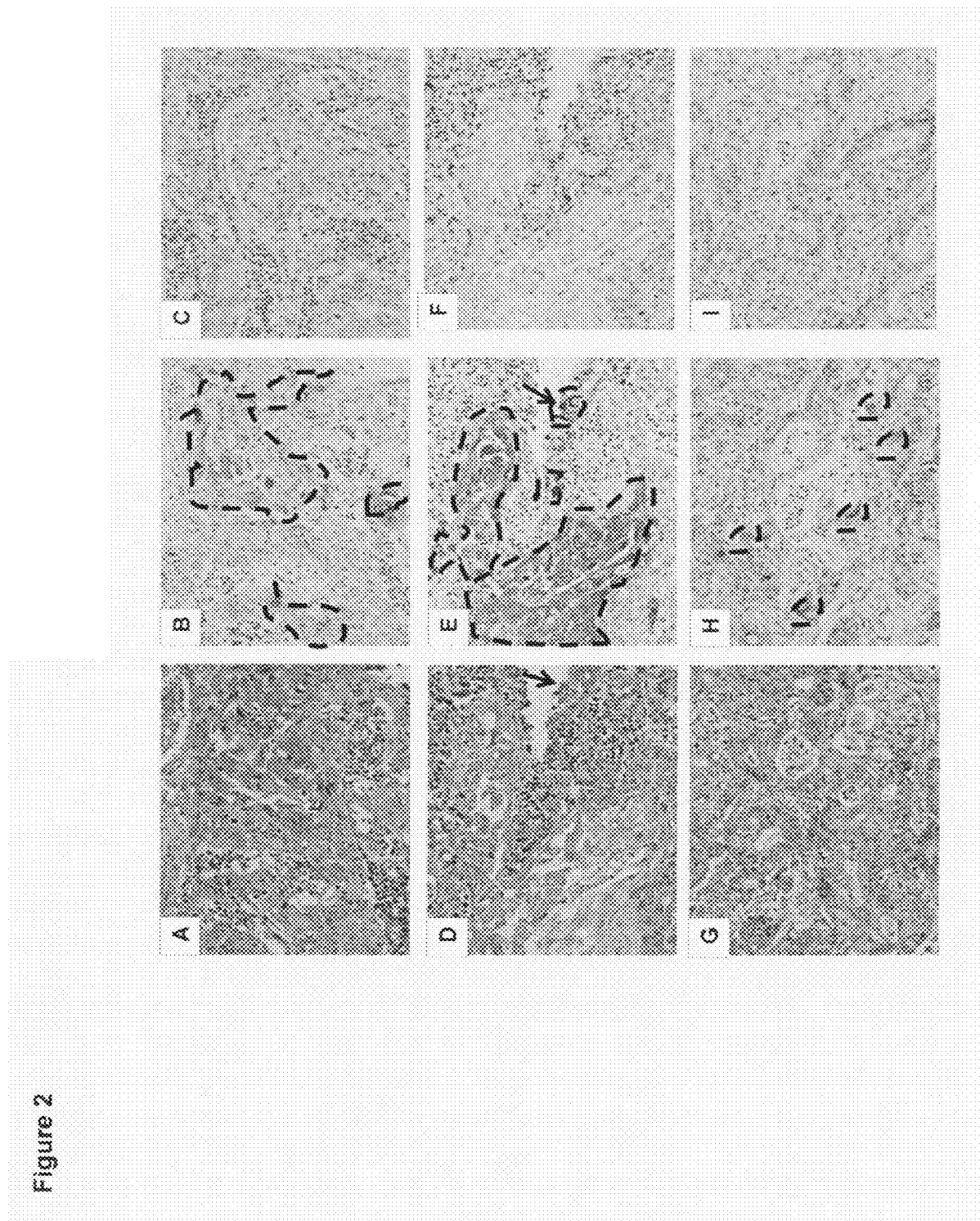
FIG. 2 Immunohistochemical staining with anti-SCCA antibody. Representative photographs of esophageal SCC (A-C), lung SCC (D-F), and gastric adenocarcinoma (G-I) are shown. A, D, and G are the hematoxylin-eosin staining, and C, F, and I are the control staining with rabbit Ig. The arrows show normal bronchial epithelia. The inner part surrounded by dot line shows the SCCA expression area. The magnification of A was X200, and that of the other 8 photographs was X100. Most SCC tissues were positive for the SCCA expression, but its expression in non-SCC tissues was rare.

The SCCA expression in SCC and non-SCC tissues were examined by immunohistochemical staining. As a result, all three esophageal SCC tissues, 4 of 5 cervical cancer tissues, and 4 of 5 lung SCC tissues were positive for SCCA. SCCA expression was not detected in any of the 5 lung adenocarcinoma or the 3 small cell carcinoma tissues. One of 6 gastric cancer tissues was positive for SCCA, but all 6 colon cancer tissues were negative. Comprehensive results are summarized in Table 1, and representative results are shown in FIG. 2.

TABLE 1

Summary of SCCA expression in various types of cancer tissues

| Types of cancer | Histology | Positive/total cases |
|---|---|---|
| Esophageal | SCC | 3/3 (100%) |
| Cervix of uterus | SCC | 4/5 (80%) |
| Lung | SCC | 4/5 (80%) |
|  | Adenocarcinoma | 0/5 (0%) |
|  | Small cell carcinoma | 0/3 (0%) |
| Gastric | Adenocarcinoma | 1/6 (17%) |
| Colon | Adenocarcinoma | 0/6 (0%) |

SCCA expression was observed in esophageal SCC (FIG. 2B) and lung SCC (FIG. 2E), and in part of the normal bronchial epithelia (pointed by arrow in figure). SCCA expression was sparsely observed in gastric adenocarcinoma (FIG. 2H).

These results indicate that most SCC tissues were positive for the SCCA expression, but its expression in non-SCC tissues was rare.

2.3 SCCA Peptide-Specific IgG in sera of Cancer Patients and HDs.

Nine SCCA-derived peptides were prepared based on their binding motif to HLA-A24 molecules (Table 2). The SCCA peptides used in the following experiments were identified by the starting position of the amino acid sequence.

TABLE 2

Table 2 The SOCA-derived peptides

| Position | Sequence | SEQ ID NO: | Binding score[a] |
|---|---|---|---|
| 10-19 | KFMFDLFQQF | 1 | 512 |
| 84-92 | QFQKLLTEF | 2 | 19.8 |
| 98-107 | AYELKIANKL | 3 | 554 |
| 107-116 | LFGEKTYLFL | 4 | 24 |
| 112-120 | TYLFLQEYL | 5 | 360 |
| 118-126 | EYLDAIKKF | 6 | 198 |
| 215-224 | QYTSFHFASL | 7 | 240 |
| 286-295 | RFKVEESYDL | 8 | 40 |
| 362-370 | EFHCNHPFL | 9 | 20 |

[a] The peptide binding score was calculated based on the predicted half-time of dissociation from HLA class I molecules as obtained from a Website (Bioinformatics and Molecular Analysis Section, Computational Bioscience and Engineering Laboratory, Division of These 9 SCCA-derived peptides were screened based on their ability to be recognized by IgG in cancer patients. Peptide-specific IgG was measured by a multiplexed flow cytometric assay (LUMINEX™ (multiplexed flow cytometric assay)). The plasma samples were derived from 35 uterine cervical SCC patients, 10 breast adenocarcinoma patients, 10 pancreatic adenocarcinoma patients, 10 gastric adenocarcinoma, and 6 colon adenocarcinoma patients. The level of fluorescence intensity was judged to be significant when exceeded 100 at an 1/100 dilution. The results are shown in Table 3.

TABLE 3

Humoral responses to the SCCA peptides

| Serum derived from patients with | | SCCA 10 | SCCA 84 | SCCA 98 | SCCA 107 | SCCA 112 | SCCA 118 | SCCA 215 | SCCA 286 | SCCA 362 |
|---|---|---|---|---|---|---|---|---|---|---|
| | | | | | Fluorescence intesity | | | | | |
| Patients | #1 | 25 | 20 | 11 | 20 | 3301 | 0 | 37 | 75 | 0 |
| Uterine cervical Ca. | #2 | 21 | 2 | 0 | 106 | 66 | 0 | 15 | 0 | 0 |
| | #3 | 11 | 0 | 0 | 51 | 575 | 0 | 25 | 21 | 0 |
| | #4 | 5 | 29 | 0 | 109 | 3138 | 0 | 68 | 229 | 0 |
| | #5 | 14 | 15 | 0 | 55 | 76 | 0 | 28 | 58 | 3 |
| | #6 | 786 | 922 | 1226 | 925 | 428 | 507 | 738 | 869 | 611 |
| | #7 | 14 | 12 | 26 | 15 | 14 | 11 | 34 | 15 | 11 |
| | #8 | 38 | 28 | 26 | 30 | 40 | 24 | 55 | 30 | 49 |
| | #9 | 76 | 67 | 58 | 84 | 94 | 82 | 106 | 93 | 90 |
| | #10 | 16 | 15 | 14 | 14 | 19 | 13 | 26 | 14 | 15 |
| | #11 | 21 | 23 | 33 | 25 | 19 | 20 | 105 | 23 | 28 |
| | #12 | 41 | 35 | 33 | 41 | 42 | 37 | 68 | 44 | 37 |
| | #13 | 22 | 23 | 397 | 33 | 26 | 20 | 60 | 29 | 25 |
| | #14 | 22 | 20 | 26 | 22 | 20 | 16 | 42 | 19 | 17 |
| | #15 | 154 | 116 | 136 | 134 | 82 | 87 | 152 | 129 | 106 |
| | #16 | 225 | 182 | 145 | 193 | 206 | 179 | 198 | 147 | 191 |
| | #17 | 50 | 56 | 72 | 65 | 53 | 45 | 87 | 63 | 56 |
| | #18 | 45 | 49 | 71 | 62 | 34 | 42 | 99 | 48 | 50 |
| | #19 | 67 | 62 | 92 | 70 | 46 | 41 | 84 | 62 | 48 |
| | #20 | 107 | 106 | 85 | 90 | 107 | 100 | 102 | 102 | 104 |
| | #21 | 22 | 19 | 28 | 25 | 22 | 20 | 45 | 21 | 22 |
| | #22 | 19 | 20 | 28 | 19 | 24 | 20 | 50 | 25 | 27 |
| | #23 | 78 | 57 | 82 | 75 | 46 | 44 | 106 | 60 | 56 |
| | #24 | 2277 | 1819 | 2650 | 1457 | 1008 | 1169 | 1822 | 1779 | 1234 |
| | #25 | 19 | 17 | 17 | 16 | 19 | 15 | 56 | 18 | 21 |
| | #26 | 88 | 128 | 166 | 147 | 72 | 106 | 132 | 97 | 83 |
| | #27 | 33 | 28 | 33 | 39 | 38 | 28 | 121 | 29 | 36 |
| | #28 | 228 | 139 | 139 | 196 | 96 | 71 | 239 | 139 | 153 |

TABLE 3-continued

Humoral responses to the SCCA peptides

| Serum derived from patients with | | SCCA 10 | SCCA 84 | SCCA 98 | SCCA 107 | SCCA 112 | SCCA 118 | SCCA 215 | SCCA 286 | SCCA 362 |
|---|---|---|---|---|---|---|---|---|---|---|
| | | | | | Fluorescence intesity | | | | | |
| | #29 | 15 | 14 | 21 | 19 | 19 | 13 | 40 | 16 | 20 |
| | #30 | 44 | 33 | 50 | 41 | 30 | 25 | 48 | 34 | 35 |
| | #31 | 107 | 108 | 107 | 108 | 123 | 101 | 147 | 104 | 133 |
| | #32 | 21 | 18 | 18 | 19 | 19 | 16 | 72 | 19 | 23 |
| | #33 | 92 | 141 | 191 | 170 | 82 | 114 | 165 | 118 | 93 |
| | #34 | 17 | 15 | 17 | 16 | 19 | 16 | 27 | 16 | 16 |
| | #35 | 17 | 18 | 21 | 20 | 21 | 19 | 31 | 21 | 21 |
| Breast Ca. | #36 | 66 | 95 | 44 | 211 | 26 | 5 | 281 | 292 | 10 |
| | #37 | 0 | 0 | 18 | 242 | 0 | 23 | 47 | 54 | 24 |
| | #38 | 27 | 31 | 12 | 146 | 0 | 1 | 142 | 95 | 8 |
| | #39 | 38 | 34 | 20 | 149 | 0 | 1 | 102 | 117 | 11 |
| | #40 | 0 | 5 | 10 | 146 | 567 | 0 | 30 | 32 | 7 |
| | #41 | 201 | 182 | 214 | 269 | 113 | 123 | 236 | 321 | 215 |
| | #42 | 0 | 11 | 12 | 219 | 62 | 14 | 76 | 47 | 19 |
| | #43 | 44 | 26 | 12 | 136 | 5924 | 7 | 81 | 58 | 10 |
| | #44 | 18 | 20 | 0 | 146 | 0 | 0 | 131 | 155 | 0 |
| | #45 | 55 | 39 | 18 | 272 | 0 | 18 | 123 | 80 | 20 |
| patients | #46 | 0 | 0 | 0 | 0 | 0 | 0 | 0 | 0 | 0 |
| Pancreas Ca. | #47 | 12 | 3 | 6 | 115 | 0 | 0 | 27 | 37 | 1 |
| | #48 | 206 | 344 | 369 | 431 | 137 | 404 | 468 | 946 | 339 |
| | #49 | 0 | 0 | 0 | 30 | 0 | 0 | 174 | 97 | 0 |
| | #50 | 311 | 0 | 0 | 29 | 280 | 0 | 10 | 0 | 0 |
| | #51 | 0 | 0 | 0 | 2 | 0 | 0 | 0 | 0 | 0 |
| | #52 | 172 | 108 | 100 | 286 | 185 | 79 | 198 | 275 | 104 |
| | #53 | 0 | 0 | 0 | 43 | 1150 | 0 | 50 | 41 | 0 |
| | #54 | 11 | 13 | 0 | 126 | 0 | 0 | 36 | 48 | 6 |
| | #55 | 0 | 0 | 0 | 0 | 0 | 0 | 6 | 24 | 0 |
| Gastric Ca. | #56 | 38 | 18 | 2 | 38 | 11506 | 0 | 152 | 243 | 0 |
| | #57 | 11 | 7 | 0 | 114 | 0 | 0 | 8 | 9 | 0 |
| | #58 | 0 | 0 | 0 | 133 | 0 | 0 | 9 | 27 | 6 |
| | #59 | 177 | 118 | 15 | 237 | 2549 | 21 | 1453 | 258 | 10 |
| | #60 | 4 | 0 | 1 | 24 | 1371 | 0 | 17 | 79 | 0 |
| | #61 | 81 | 102 | 8 | 282 | 0 | 5 | 47 | 286 | 1 |
| | #62 | 0 | 0 | 0 | 37 | 195 | 0 | 0 | 0 | 0 |
| | #63 | 0 | 0 | 0 | 29 | 0 | 0 | 0 | 7 | 0 |
| | #64 | 9 | 7 | 0 | 67 | 0 | 2 | 44 | 40 | 0 |
| | #65 | 0 | 0 | 0 | 72 | 1312 | 0 | 10 | 37 | 0 |
| Colon Ca. | #66 | 5 | 0 | 0 | 40 | 257 | 2 | 16 | 4 | 0 |
| | #67 | 79 | 47 | 0 | 49 | 0 | 0 | 74 | 35 | 0 |
| | #68 | 0 | 0 | 0 | 0 | 0 | 0 | 0 | 0 | 0 |
| | #69 | 2 | 0 | 0 | 20 | 317 | 0 | 41 | 8 | 0 |
| | #70 | 17 | 0 | 0 | 91 | 105 | 0 | 59 | 16 | 1 |
| | #71 | 6 | 8 | 26 | 70 | 0 | 17 | 23 | 45 | 19 |
| Total | | 12/71 | 14/71 | 12/71 | 27/71 | 23/71 | 7/71 | 24/71 | 19/71 | 10/71 |
| Healthy Donors | #1 | 0 | 0 | 0 | 53 | 607 | 0 | 0 | 21 | 0 |
| | #2 | 68 | 79 | 35 | 297 | 52 | 47 | 164 | 219 | 37 |
| | #3 | 0 | 0 | 0 | 67 | 0 | 0 | 14 | 9 | 0 |
| | #4 | 0 | 0 | 0 | 0 | 0 | 0 | 0 | 0 | 0 |
| | #5 | 8 | 0 | 0 | 331 | 387 | 0 | 87 | 239 | 0 |
| | #6 | 0 | 0 | 0 | 0 | 0 | 0 | 0 | 2 | 0 |
| | #7 | 0 | 0 | 0 | 0 | 990 | 0 | 0 | 0 | 0 |
| | #8 | 345 | 332 | 361 | 454 | 496 | 324 | 427 | 516 | 283 |
| | #9 | 34 | 33 | 39 | 246 | 1396 | 37 | 41 | 100 | 29 |
| | #10 | 0 | 0 | 0 | 106 | 0 | 0 | 134 | 138 | 0 |
| Total | | 1/10 | 1/10 | 1/10 | 5/10 | 5/10 | 2/10 | 3/10 | 4/10 | 1/10 |

IgG reactive to a corresponding peptide was judged to be significant when the fluoresence intensity at a 1:100-diluted sample was m than 100. The significant values are underlined.

Figure 3:
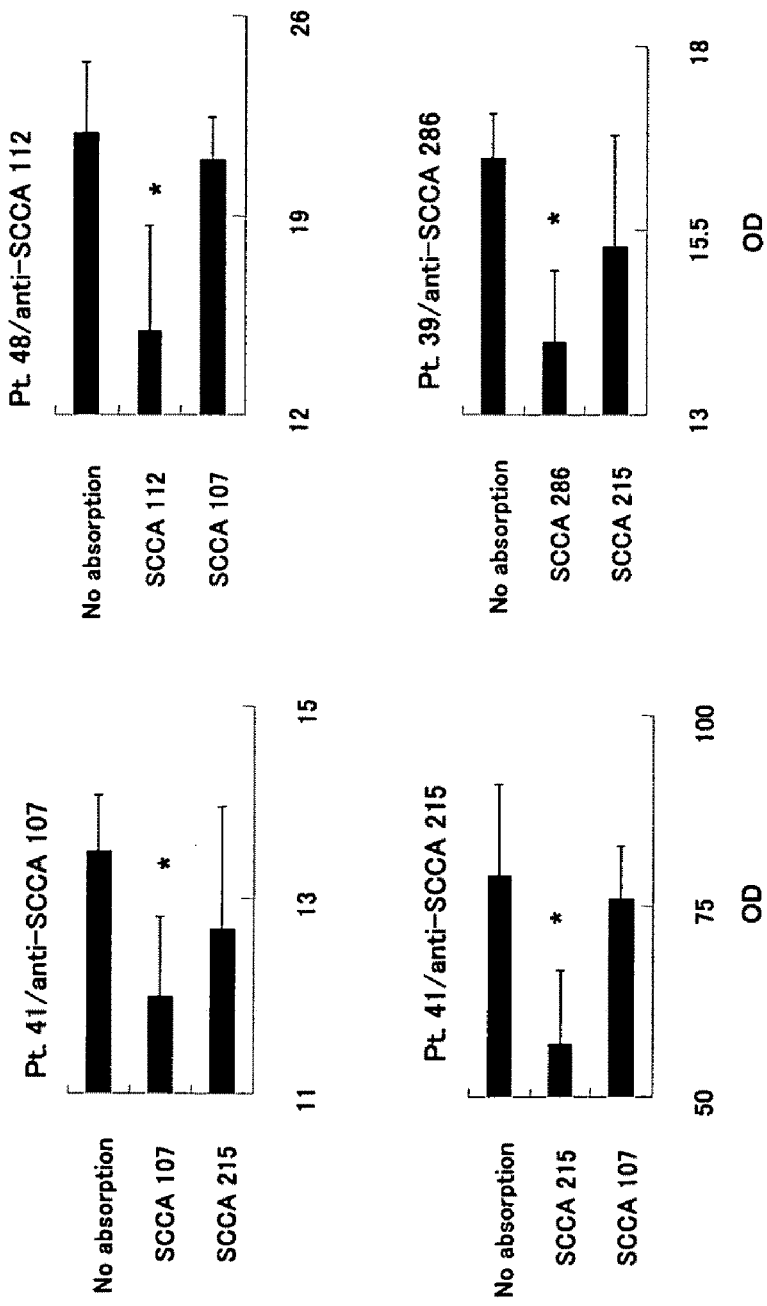
FIG. 3 Peptide-specific IgG in sera of cancer patient. Asterisks indicate P<0.05, as determined by a two-tailed Student's t-test. Specificity of IgG reactive to the specific peptides was confirmed by absorption assay with the corresponding peptides.

IgG reactive to the $SCCA_{107}$, $SCCA_{112}$, $SCCA_{215}$, and $SCCA_{286}$ peptides was more frequently detected in the patients' sera than was IgG reactive to the other 5 peptide. Their frequencies were $^{27}/_{71}$, $^{23}/_{71}$, $^{24}/_{71}$, and $^{19}/_{71}$, respectively. The sera from 10 HDs also showed similar results. As illustrated in FIG. 3, the specificity of IgG reactive to each of the $SCCA_{107}$, $SCCA_{112}$, $SCCA_{215}$, and $SCCA_{286}$ peptides was confirmed by absorption assay. Namely, the level of IgG reactive to each of the 4 SCCA peptides was absorbed by culturing the sample in corresponding SCCA peptide-coated wells, but not in irrelevant SCCA peptide-coated wells.

Based on these findings, we focused on the following peptides in the subsequent experiments: $SCCA_{107}$, $SCCA_{112}$, $SCCA_{215}$, and $SCCA_{286}$.

2.4 Induction of Peptide-Specific CTLs from Cancer Patients.

Figure 4:
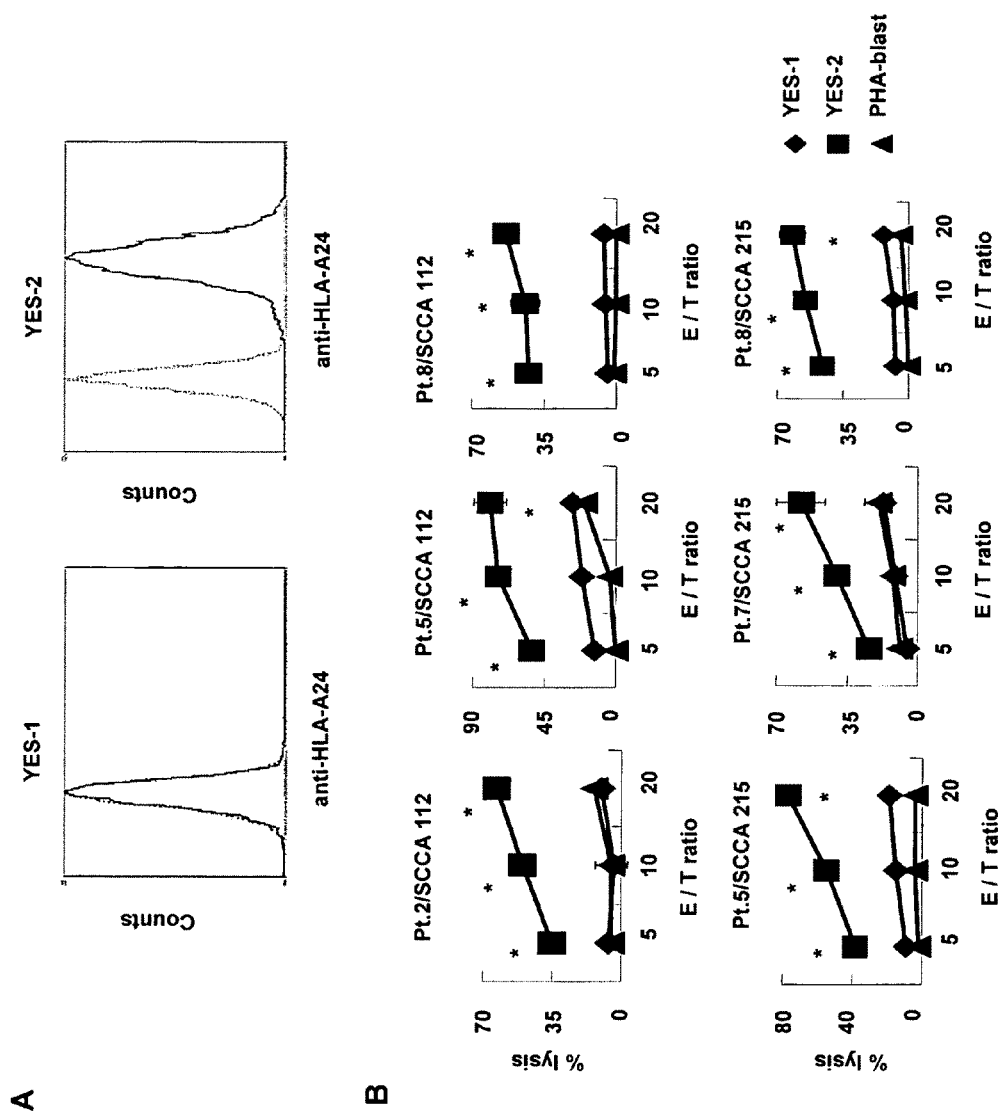
FIG. 4A Expression of HLA-A24 molecules in two esophageal SCC cell lines, YES-1 and YES-2. The dotted lines represent staining without the first mAb. YES-1 was confirmed to be HLA-A24$^-$ and YES-2 was HLA-A24$^+$.
FIG. 4B Cytotoxicity of SCCA peptide-induced CTLs. A standard 6-h $^{51}$Cr-release assay was carried out to test SCCA peptide-induced CTLs for their cytotoxicity against three targets: YES-1 (HLA-A24$^-$, SCCA$^+$), YES-2 (HLA-A24$^+$, SCCA$^+$), and PHA-stimulated T-cell blasts (HLA-A24$^+$, SCCA$^-$) The representative results of four cancer patients (Pts 2, 5, 7, and 8) are shown. Asterisks indicate P<0.05, as determined by a two-tailed Student's t-test. Here, SCCA peptide-stimulated CTLs showed a higher level of cytotoxicity against YES-2 than against YES-1 and PHA-stimulated T-cell blasts.

Whether or not the $SCCA_{107}$, $SCCA_{112}$, $SCCA_{215}$, and $SCCA_{286}$ peptides had the potential to induce peptide-specific CTLs from the PBMCs of 20 HLA-A24$^+$ cancer patients and 8 HLA-A24$^+$ healthy donors was investigated. The group of twenty cancer patients consisted of 4 esophageal SCC patients, 4 cervical SCC patients, 4 lung cancer patients (2 adenocarcinomas, one small cell carcinoma, and one squamous cell carcinoma), 4 gastric adenocarcinoma patients, and 4 colon adenocarcinoma patients. The assay was carried out in quadruplicate. The cultured cells in one well were separated into 4 wells, and two wells were used for the SCCA peptide-pulsed C1R-A24 cells, and the other two were used for the HIV peptide-pulsed C1R-A24 cells. The successful induction of peptide-specific CTLs was judged to be positive when the supernatant of at least one well showed more than 50 pg/ml IFN-γ production with a statistically significant difference (p value of <0.05). The results which showed the best response are shown, and the background IFN-γ production in response to an HIV peptide was subtracted. Results are shown in Table 4.

ity against cancer cells was investigated. As shown in FIG. 4A, although both YES-1 and YES-2 were SCCs, only the YES-2 was positive for HLA-A24 molecules. Therefore, YES-2 was used as a positive target expressing both the SCCA and the HLA-A24 molecules.

Here, SCCA peptide-stimulated CTLs from 4 SCC cancer patients (Pts 2, 5, 7, and 8) showed a higher level of cytotoxicity against YES-2 than against YES-1 and HLA-A24$^+$ PHA-stimulated T-cell blasts (FIG. 4B). The PBMCs stimulated with the HIV peptide, used as a negative control, did not show any cytotoxicity (data not shown).

TABLE 4

Reactivity of SCCA peptide-stimulated PBMCs from HLA-A24$^+$ healty donors and cancer patients

| | | Peptide | | | | |
|---|---|---|---|---|---|---|
| PBMCs derived from | Types of cancer | SCCA 107 | SCCA 112 | SCCA 215 | SCCA 286 | EBV |
| | | IFN-γ Production (pg/ml) | | | | |
| Patient # | | | | | | |
| 1 | Esophagus | — | — | — | — | 748 |
| 2 | Esophagus | 84 | 106 | 85 | — | 491 |
| 3 | Esophagus | — | — | — | — | 879 |
| 4 | Esophagus | — | — | — | 97 | — |
| 5 | Cervix of uterus | — | 678 | 117 | — | — |
| 6 | Cervix of uterus | 105 | — | 96 | — | — |
| 7 | Cervix of uterus | — | — | 210 | 169 | — |
| 8 | Cervix of uterus | — | 61 | 541 | — | 67 |
| 9 | Lung (small cell) | — | 321 | — | — | — |
| 10 | Lung (adeno) | — | 837 | 362 | — | — |
| 11 | Lung (SCC) | — | 75 | 83 | — | — |
| 12 | Lung (adeno) | — | 319 | — | — | 62 |
| 13 | Stomach | 500 | 148 | — | — | — |
| 14 | Stomach | — | — | 129 | — | 109 |
| 15 | Stomach | — | 958 | 340 | — | 291 |
| 16 | Stomach | — | — | — | — | 61 |
| 17 | Colon | — | — | — | — | — |
| 18 | Colon | — | 171 | 121 | — | — |
| 19 | Colon | — | 115 | 371 | — | — |
| 20 | Colon | — | 430 | 118 | — | 70 |
| Total | | 3/20 | 12/20 | 12/20 | 3/20 | 9/20 |
| Healthy donor # | | | | | | |
| 1 | | — | — | — | — | — |
| 2 | | — | — | — | — | — |
| 3 | | — | — | — | — | — |
| 4 | | — | — | — | — | 635 |
| 5 | | — | 1239 | — | — | 51 |
| 6 | | — | — | — | — | — |
| 7 | | 259 | — | — | — | — |
| 8 | | — | — | — | — | 73 |
| Total | | 1/8 | 1/8 | 0/8 | 0/8 | 3/8 |

The PBMCs from HLA-A24$^+$ cancer patients and healthy donors were stimulated in vitro with the Indicated SCCA peptides as described in Materials and Methods. On day 15, the cultured PBMCs were tested for their reactivity to C1R-A24 cells, which were pre-pulsed with a corresponding peptide in quadruplicate. Values represent the means of IFN-γ production. Background IFN-γ proudction in response to the HIV peptide was subtracted. Significant values (P < 0.05 by two-tailed Student's t-test) are shown.

It was found that peptide-specific CTLs were induced from the PBMCs of 12 of 20 cancer patients when either the SCCA$_{112}$ or the SCCA$_{215}$ peptide was used for in vitro stimulation. Each of the SCCA$_{107}$ and SCCA$_{286}$ peptides induced peptide-specific CTLs in 3 of 20 cancer patients. On the other hand, these 4 SCCA peptides were less efficient at inducing peptide-specific CTLs from the PBMCs of 8 healthy donors.

These results indicate that both the SCCA$_{112}$ and SCCA$_{215}$ peptides can efficiently induce peptide-specific CTLs in HLA-A24$^+$ patients with SCC or non-SCC.

2.5 SCCA Peptide-Specific and CD8$^+$ T Cell-Dependent Cytotoxicity Against Cancer Cells.

Figure 5:
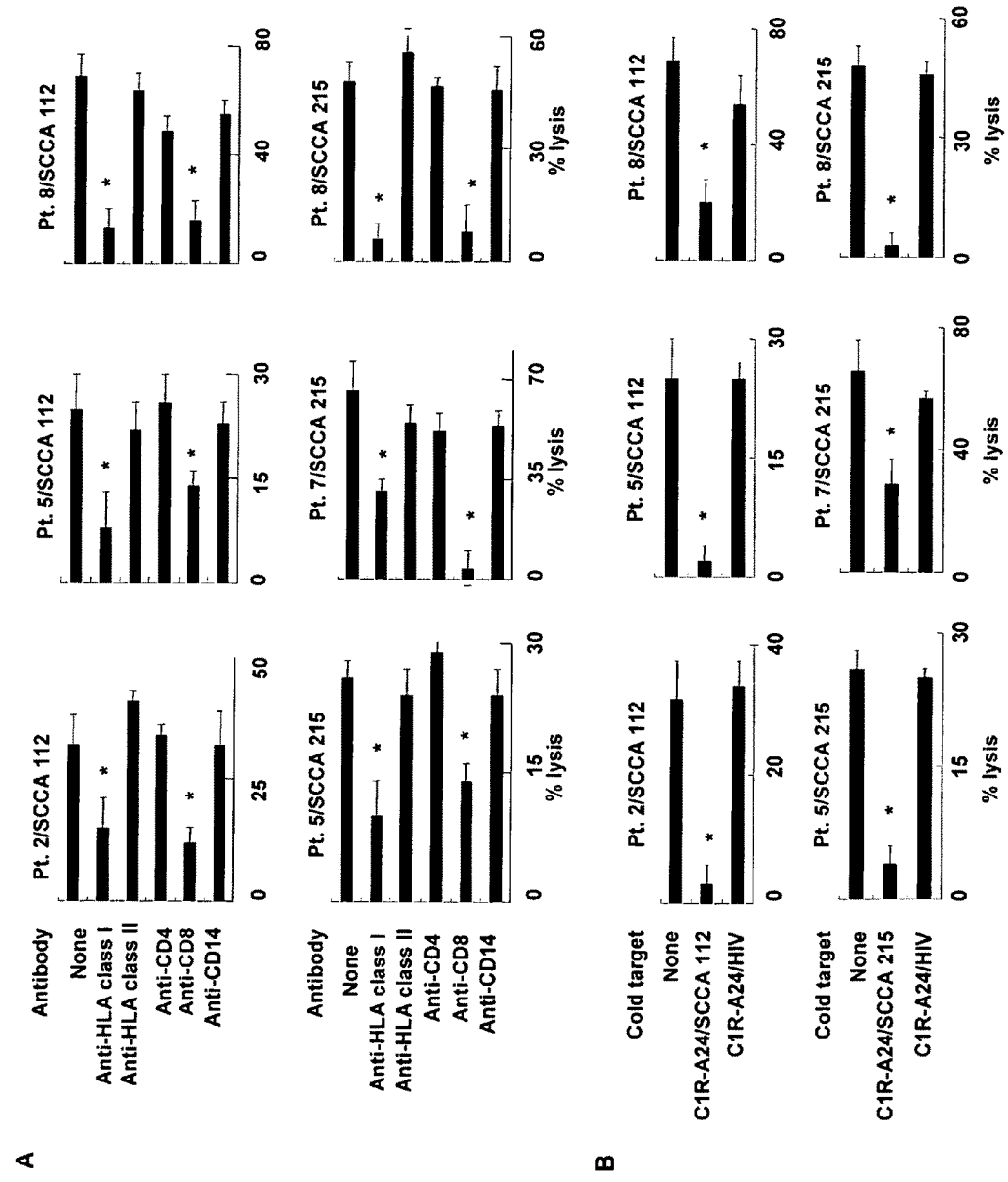
FIG. 5A HLA-class I restricted and CD8$^+$ T cell-dependent cytotoxicity of SCCA peptide reactive CTL. YES-2 (HLA-A24$^+$, SCCA$^+$) was used as target cell. Asterisks indicate P<0.05, as determined by a two-tailed Student's t-test. The cytotoxicity of the CTLs, which induced from PBMC by stimulation with SCCA, against YES-2 was significantly inhibited by the addition of anti-HLA-class I or anti-CD8 mAb.
FIG. 5B Peptide specificity of the cytotoxic activity of SCCA peptide reactive CTL. Asterisks indicate P<0.05, as determined by a two-tailed Student's t-test. The cytotoxicity was diminished by the addition of the corresponding SCCA peptide-pulsed C1R-A24 cells.

Whether or not SCCA$_{112}$ peptide- or SCCA$_{215}$ peptide-stimulated CTLs from SCC patients could exhibit cytotoxic- It was then determined what cell types were responsible for the cytotoxicity. The cytotoxicity of the SCCA peptide-stimulated PBMCs against YES-2 was significantly inhibited by the addition of anti-HLA-class I or anti-CD8 mAb, but not by the addition of other mAbs (FIG. 5A). In a cold-inhibition assay, the cytotoxicity of the SCCA peptide-stimulated PMBCs was inhibited by the addition of the corresponding SCCA peptide-pulsed, unlabeled C1R-A24 cells, but not by the addition of HIV peptide-pulsed unlabeled C1R-A24 cells (FIG. 5B).

As is the case with SCC patients, SCCA$_{112}$ peptide- or SCCA$_{215}$ peptide-stimulated CTLs from adenocarcinoma patients (Pts 10, 15, and 20) exhibited cytotoxicity against YES-2 cells in an HLA class I-restricted manner (data not shown).

These results suggest that the cytotoxicity of SCCA derived peptide-stimulated PBMCs against YES-2 could largely be due to HLA class I-restricted and SCCA peptide-specific CD8+ T cells.

3. CONCLUSION

According to the results shown above, SCCA derived peptides, especially $SCCA_{112}$ peptide and $SCCA_{215}$ peptide can effectively induce CTLs that are reactive against SCC in HLA-A24 positive SCC patient.

The invention claimed is:

1. An isolated peptide, which consists of the amino acid sequence of SEQ ID NO: 5 or 7.

2. An isolated peptide, comprising the amino acid sequence of SEQ ID NO: 5 or 7, wherein said isolated peptide is a peptide fragment of squamous cell carcinoma antigen having the amino acid sequence of SEQ ID NO: 11, capable of binding to an HLA-A24 molecule and recognized by the cellular immune system and wherein said peptide fragment consists of no more than 14 amino acid residues.

* * * * *